United States Patent [19]

Kogure et al.

[11] 4,042,617
[45] Aug. 16, 1977

[54] PROCESS FOR PREPARING A 2-METHYL-(SUBSTITUTED ARYL)-PYRUVIC ACID COMPOUND

[75] Inventors: Katsura Kogure, Kawagoe; Noriyoshi Sueda, Tokyo; Sizuo Himoto, Kawagoe; Youziro Yoshino, Tokyo; Kunio Nakagawa, Kawagoe, all of Japan

[73] Assignee: Nisshin Flour Milling Co., Ltd., Tokyo, Japan

[21] Appl. No.: 599,773

[22] Filed: July 28, 1975

[30] Foreign Application Priority Data

July 27, 1974 Japan .................................. 49-85620
July 29, 1974 Japan .................................. 49-86003

[51] Int. Cl.$^2$ .................... C07C 51/09; C07C 63/333; C07C 67/30; C07C 69/76
[52] U.S. Cl. ............................. 260/469; 260/348.59; 260/473 R; 260/473 A; 260/515 R; 260/515 A; 260/517; 260/520 R; 260/520 B; 260/348.51
[58] Field of Search .................. 260/473 A, 483, 469, 260/515 R, 473 R, 520 R, 515 A, 517

[56] References Cited

U.S. PATENT DOCUMENTS

| 3,048,622 | 8/1962 | Stansbury et al. | 260/483 |
| 3,919,304 | 11/1975 | Rossi | 260/473 A |
| 3,925,458 | 12/1975 | Kogure et al. | 260/473 A |

*Primary Examiner*—Jane S. Myers

[57] ABSTRACT

A process for preparing 3-methyl-3-(substituted aryl)-pyruvic acid compounds by treating a glycidic acid ester compound of the formula,

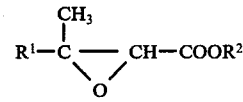

wherein R$^1$ is a 4-biphenylyl, 4-clyclohexylphenyl, 3-phenoxyphenyl, 4'-fluoro-4-biphenylyl, 2-fluoro-4-biphenylyl or 3-benzoylphenyl group and R$^2$ is a lower alkyl group or its corresponding free acid with a Lewis acid to form a 2-hydroxy-3-(substituted aryl)-3-butenoic acid ester and treating the resulting ester in an alcohol with an alkali metal alcoholate to form the pyruvic acid compounds. If desired, the pyruvic acid compounds can then be saponified to compounds of the formula,

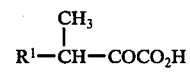

wherein R$^1$ is as previously defined and which compounds are useful as anti-inflammatory agents.

3 Claims, No Drawings

PROCESS FOR PREPARING A 2-METHYL-(SUBSTITUTED ARYL)-PYRUVIC ACID COMPOUND

This invention relates to a process for preparing 3-methyl-3-(substituted aryl)-pyruvic acid compounds through new intermediates starting with certain glycidic acid esters. The products obtained by the invention are new compounds useful for preparation of anti-inflammatorily effective 2-(substituted aryl)-propionic acids.

In accordance with the present invention, there is provided a process which comprises treating a glycidic acid ester derivative of the general formula (I)

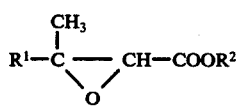
(I)

wherein $R^1$ represents 4-biphenylyl, 4-cyclohexylphenyl, 3-phenoxyphenyl, 4'-fluoro-4-biphenylyl, 2-fluoro-4-biphenylyl or 3-benzoylphenyl group, and $R^2$ is a lower alkyl group, with a Lewis acid, thereby to form a 2-hydroxy-3-(substituted aryl)-3-butenoic acid ester of the general formula (II)

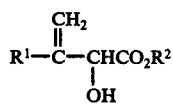
(II)

wherein $R^1$ and $R^2$ are same as above; treating the resulting ester (II) in an alcohol with an alkali metal alcoholate to form a 3-methyl-3-(substituted aryl)-pyruvic acid ester compound of the general formula (III)

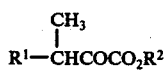
(III)

wherein $R^1$ and $R^2$ are same as above; and then hydrolyzing the thus formed ester to form a 3-methyl-3-(substituted aryl)-pyruvic acid of the general formula (IV)

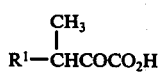
(IV)

wherein $R^1$ is as defined previously. By oxidizing the products thus formed according to the present process, it becomes possible to obtain in an industrially easy manner and in good yields a 2-(substituted phenyl)-propionic acid, which is useful as an anti-inflammatory agent, represented by the general formula

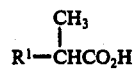
(V)

wherein $R^1$ is as defined previously.

According to the first step of the present process, a unique electron-withdrawing reaction is brought about by the treatment of a compound of the aforesaid general formula (I) with a Lewis acid in an amount greater than an approximately equimolar quantity, whereby there is obtained a product of the aforesaid general formula (II) in a substantially quantitative yield. Such reaction is a novel reaction which has heretofore not been disclosed yet in any literatures. Lewis acids which can be used in carrying and the process of this invention are boron trifluoride, aluminum chloride, zinc chloride or the like. The reaction of this step is usually carried out in solvent, and there may be used preferably such non-protonic polar solvents, for example, as dimethylsulfoxide or dimethylformamide. Relatively high boiling ethers, for example isopropyl ether, may also be used as the solvent. A practical reaction temperature which can be used to carry out the process for the formation of compounds of the aforesaid general formula (II) is from 0° to 100° C. A reaction time of from 30 minutes to 1 hour is normally sufficient. After completion of the reaction, isolation and purification of the reaction product obtained may be carried out quite easily by ordinary procedures.

The compounds of the formula (I), which are used as the starting compounds in the process of the present invention, may be prepared, for example, by reacting a corresponding acetophenone derivative of the formula $R^1$—COCH$_3$ (wherein $R^1$ is as defined previously) with a corresponding α-halogenoacetate of the formula XCH$_2$COOR$^2$ (wherein $R^2$ is as defined previously). This reaction is carried out under the conditions for Darzen's condensation, and the condensing agent used therein includes such compounds as sodium methoxide, sodium ethoxide, sodium isopropoxide, sodium amide and the like. The reaction is preferably carried out in an atmosphere of inert gas and under anhydrous conditions.

In the second step of the process of the present invention, a compound of the general formula (II) is treated in alcohol by heating the compound with an alkali metal alcoholate to obtain a compound of the general formula (III). The compounds which can be obtained in this step are novel compounds which have not been disclosed in any existing literatures. A physical property and spectral data of such exemplary novel compounds, for example, those as having a methyl group as $R^2$, are as shown below.

| $R^1$ | IR (cm$^{-1}$) | NMR (δ ppm) | Physical property |
|---|---|---|---|
| 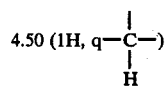 | 1723 1278 1120 1044 | 1.47 (3H, d—C—) 3.73 (3H, S—CO$_2$Me)<br><br>4.50 (1H, q—C—)<br>H | m.p. 71.1 – 72.2° C |

-continued

| R¹ | IR (cm⁻¹) | NMR (δ ppm) | Physical property |
|---|---|---|---|
| (biphenyl) | 1728 1275 1115 1043 765 732 | 1.48 (3H, d—C(CH₃)—) 3.72 (3H, S—CO₂Me)  4.54 (1H, q—C(H)—) | m.p. 84.5 – 86.5° C |
| (4-F-biphenyl) | 1730 1502 1278 1045 821 | 1.49 (3H, d—C(CH₃)—) 3.74 (3H, S—CO₂Me)  4.55 (1H, q—C(H)—) | m.p. 100.0 – 101.6° C |
| (phenoxy-tolyl) | 1731 1580 1489 1254 1042 | 1.42 (3H, d—C(CH₃)—) 3.72 (3H, S—CO₂Me)  4.44 (1H, q—C(H)—) | Pale yellow oil |

As alkali metal component of the alkali metal alcoholate used in this step, there may be mentioned sodium or potassium alcoholate. Suitable as alcohols which can be used are methanol, ethanol, isopropanol and tertiary butanol. The reaction temperature is favorably 60° to 90° C., and the reaction time is suitably from 30 minutes to 1 hour. The compound of the general formula (III), which has been obtained in the second step of the present process, is high in purity and hence may be used, as it is, in the subsequent reaction in the present process. The reaction which forms the compound of the general formula (III) from the compound of the general formula (II), is an entirely novel reaction which has not been disclosed in any existing literature.

In the third step of the process of the present invention, the compound represented by the general formula (III) is hydrolyzed to obtain a compound represented by the general formula (IV). This hydrolysis reaction is preferably effected in an alkaline environment, though the reaction may proceed either in an alkaline or acidic environment. Preferably usable as a solvent in the hydrolysis reaction is methanol or ethanol, and sodium hydroxide or potassium hydroxide is preferably used as the alkali to effect the reaction in the alkaline environment. The reaction temperature is conveniently from 20° to 30° C., though the reaction may be carried out at a temperature ranging from 0° to 100 ° C., and the reaction time is suitably from 40 minutes to 1 hour, though the time may range over a period of from 30 minutes to 5 hours. The compounds of the general formula (IV), which are obtained in the third step of the present process, are also novel compounds, a physical property and spectral data of such exemplary compounds are as shown below.

| R¹ | IR (cm⁻¹) | NMR(δ ppm) | Physical property |
|---|---|---|---|
| (cyclohexyl-phenyl) | 1702 1290 1131 827 | 1.43 (3H, d, —C(CH₃)—)  4.53 (1H, q, —C(H)—) | m.p. 100.5 – 102.1° C. |
| (biphenyl) | 1732 1701 1260 918 762 726 | 1.50 (3H, d, —C(CH₃)—) | m.p. 141.0 – 143.2° C. |

-continued

| R¹ | IR (cm⁻¹) | NMR(δ ppm) | Physical property |
|---|---|---|---|
| 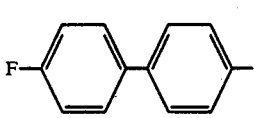 | 1732 1700 1499 1240 1168 821 | 4.56 (1H, q, −C−H)<br><br>CH₃<br>1.48 (3H, d, −C−) | m.p. 144.7 − 145.9° C. |
| 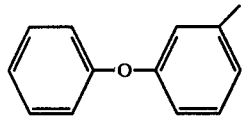 | 1723 1580 1489 1250 | 4.58 (1H, q, −C−H)<br><br>CH₃<br>1.44 (3H, d, −C−)<br><br>4.53 (1H, q, −C−H) | Colorless oil |

Subsequent to carrying out the process of the present invention, the compound of the general formula (IV) may be oxidized in an aqueous alkali solution with hydrogen peroxide to obtain a compound of the general formula (V). In this oxidation step, the reaction temperature is 10° to 25° C., and the reaction time is suitably 10 to 20 hours. In a case where a process involving the first step through the final oxidation step is intended to be put into operation on a commercial scale, it is not always necessary to individually isolate the compound of the general formula (II) and the compound of the general formula (III), which have been formed in the aforesaid first and second steps, respectively, after completion of the respective steps. That is, immediately after completion of the heat treatment in alcohol of the compound of the general formula (II) with an alkali metal alcoholate, the hydrolysis of the resulting compound of the general formula (III) is effected and, after distilling off the alcohol, the oxidation reaction of the resulting compound of the general formula (IV) with hydrogen peroxide is carried out with addition thereto of water, followed by acid treatment, whereby a 2-(substituted aryl)-propionic acid represented by the general formula (V) is obtained. Thus, as a process for preparing the 2-(substituted aryl)-propionic acid on an industrial scale, the process illustrated above is extremely advantageous in that all the reactions may be effected in a single reactor, the operational procedure is quite easy and the desired product is obtained in high yields. The compound of the general formula (V) thus obtained may be converted, if desired, into non-toxic organic and inorganic salts thereof.

The present invention is illustrated below with reference to the following examples.

EXAMPLE 1

Methyl 2-Hydroxy-3-(4-cyclohexylphenyl)-3-butenoate

A solution of 40 g of 4-cyclohexylacetophenone and 43.2 g of methyl chloroacetate in a solvent mixture comprising 50 ml of n-hexane and 50 ml of benzene was vigorously stirred, and 27.8 g of sodium methoxide was gradually added thereto in a nitrogen stream at below 5° C. over a period of 1 hour. After stirring at 5° C. for 2 hours and at room temperature for 1 hour, the mixture was refluxed under heating with stirring for 30 minutes. After cooling, hexane was added to the mixture to separate an organic layer. The organic layer was washed with water and dried, and the organic layer was removed therefrom by distillation under reduced pressure to obtain 50 g of methyl 3-methyl-3-(4-cyclohexylphenyl)-glycidate in the form of oil. The yield was 91% (calculated value based on 4-cyclohexylacetophenone).

Elementary analysis: for C₁₇H₂₂O₃ (274) — Calculated: C : 74.42%, H : 8.08%. Found: C : 74.61%, H : 8.30%.

IR (cm⁻¹) 1755, 1735, 1210, 836.
NMR (δ ppm) 1.73 (3H, s,

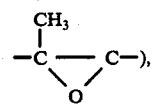

3.80, 3.42 (3H, s, s, −CO₂CH₃), 3.45, 3.63 (1H, s, s,

To a solution of 11 g of methyl 3-methyl-3-(4-cyclohexylphenyl)-glycidate in 40 ml of dimethylsulfoxide was added with stirring and ice-cooling 6 ml of a 47% ether solution of boron trifluoride. The mixture was brought back to room temperature and stirred for 2 hours, and was then poured into water and extracted with ethyl acetate. The ethyl acetate layer was successively washed with water, aqueous sodium bicarbonate solution, water and saturated aqueous sodium chloride solution, and then dried over anhydrous magnesium sulfate. The ethyl acetate was removed by distillation under reduced pressure to obtain 10 g of methyl 2-hydroxy-3-(4-cyclohexylphenyl)-3-butenoate. The yield was 91%.

Elementary analysis: for $C_{17}H_{22}O_3$ (274) — Calculated: C : 74.42%, H : 8.08%. Found: C : 74.59%, H : 8.29%.

IR (cm$^{-1}$) 3470, 1730, 1214, 1110, 1078.

NMR (δ ppm) 3.70 (3H, s, —CO$_2$Me), 5.03 (1H, s,

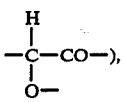), 5.35, 5.46 (2H, s, s,

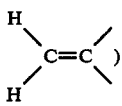)

EXAMPLE 2

Methyl 2-Hydroxy-3-(3-phenoxyphenyl)-3-butenoate

A solution of 19.4 g of 3-phenoxyacetophenone and 21.6 g of methyl chloroacetate in 40 ml of benzene was vigorously stirred, and 13.9 g of sodium methoxide was gradually added thereto in a nitrogen stream at 5°–6° C. over a period of 1 hour. After stirring at that temperature for 1 hour, the mixture was brought back to room temperature and then stirred for an additional 1 hour. Subsequently, the mixture was refluxed under heating with stirring for 1 hour and then cooled. To the mixture were added benzene and water, thereby effecting benzene extraction. The benzene layer was washed with water and dried over anhydrous sodium sulfate and, thereafter the benzene was removed therefrom by distillation under reduced pressure to obtain 21.0 g of methyl 3-methyl-3-(3-phenoxyphenyl)-glycidate in the form of oil. The yield was 81%.

Elementary analysis: for $C_{17}H_{16}O_4$ (284) — Calculated: C: 71.82%, H: 5.67%. Found: C: 71.69%, H: 5.51%.

IR (cm$^{-1}$) 1754, 1730, 1580, 1228.

NMR (δ ppm) 1.68, 1.72 (3H, s, s,

), 3.47, 3.79 (3H, s, s, —CO$_2$CH$_3$), 3.42, 3.63 (1H, s, s,

)

To a solution of 8.0 g of methyl 3-methyl-3-(3-phenoxyphenyl)-glycidate in 100 ml of dimethylsulfoxide was added with stirring and ice-cooling 30 ml of an ether solution of boron trifluoride. After stirring at room temperature for 20 hours, the mixture was poured into water and extracted with ethyl acetate. The ethyl acetate layer was successively washed with water, aqueous sodium bicarbonate solution and water, and then dried over anhydrous magnesium sulfate. The ethyl acetate was removed by distillation under reduced pressure, and the residue weighing 8.0 g was purified by silica gel column chromatography to obtain 4.7 of methyl 2-hydroxy-3-(3-phenoxyphenyl)-3-butenoate in the form of oil. The yield was 59% (calculated value).

Elementary analysis: for $C_{17}H_{16}O_4$ (284) — Calculated: C: 71.82%, H: 5.67%. Found: C: 71.68%, H: 5.50%.

IR (cm$^{-1}$) 3480, 1733, 1584, 1570, 1486, 1222.

MNR (δ ppm) 3.68 (3H, s, —CO$_2$Me), 5.00 (1H, s,

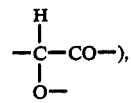), 5.43, 5.48 (2H, s, s,

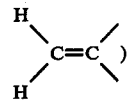)

EXAMPLE 3

Methyl 2-Hydroxy-3-(4-biphenylyl)-3-butenoate

A solution of 14.0 g of 4-acetylbiphenyl and 15.4 g of methyl chloroacetate in a solvent mixture comprising 60 ml of benzene and 30 ml of ether was vigorously stirred, and 8.5 g of sodium methoxide was gradually added thereto in a nitrogen stream at 8° C. or below over a period of 30 minutes. The mixture was stirred at 10° C. for 1 hour, at 25° C. for 1 hour and at refluxing temperature for 1 hour, and was then cooled. The mixture was charged with ether to separate an organic layer which was then washed with water and dried. The organic solvents were removed by distillation under reduced pressure to obtain 15.0 g of methyl 3-methyl-3-(4-biphenylyl)-glycidate in the form of powder, m.p. 74.7°–77.0° C. The yield was 71%.

IR (cm$^{-1}$) 1748, 1208, 1081, 770.

NMR (δ ppm) 1.77, 1.79 (3H, s, s,

), 3.46, 3.82 (3H, s, s, —CO$_2$CH$_3$), 3.50, 3.70 (1H, s, s,

)

To a solution of 8.0 g methyl 3-methyl-3-(4-biphenylyl)-glycidate in a solvent mixture comprising 30 ml of dimethylsulfoxide and 20 ml of benzene was added dropwise with ice-cooling 7 ml of a 47% ether solution of boron trifluoride. The mixture was brought back to room temperature and, after stirring for 3 hours, was poured into water and then extracted with benzene. The benzene layer was successively washed with water, aqueous sodium bicarbonate solution and water, and the dried over anhydrous magnesium sulfate. The benzene was removed by distillation under reduced pressure to obtain 6.8 g of methyl 2-hydroxy-3-(4-biphenylyl)-butenoate in the form of semi-crystal. The yield was 85% (calculated value).

Elementary analysis: for $C_{17}H_{16}O_3$ (286) — Calculated: C: 76.10%, H: 6.01%. Found: C: 75.91%, H: 6.31%.

IR (cm$^{-1}$) 3460, 1731, 1596, 1242, 1208, 1112, 1078, 843.

NMR (δ ppm) 3.72 (3H, s, —CO$_2$Me), 5.10 (1H, s,

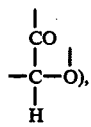

5.44, 5.56 (2H, s, s,

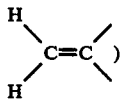

Example 4
Methyl 2-Hydroxy-3-(2-fluoro-4-biphenylyl)-3-butenoate

A solution of 19.0 g of 4-acetyl-2-fluorobiphenyl and 19.2 g of methyl chloroacetate in a solvent mixture comprising 40 ml of benzene and 20 ml of dimethylformamide was vigorously stirred, and 10.6 g of sodium methoxide was gradually added in a nitrogen stream at below 8° C. over a period of 1 hour. After stirring at 10° C. for 1 hour, at 25° C. for 1 hour and at 60° C. for 1 hour, the mixture was cooled and charged with benzene and water, thereby effecting benzene extraction. The benzene layer was washed with water, dried over anhydrous magnesium sulfate and then the benzene was removed therefrom by distillation under reduced pressure to obtain 20.2 g of methyl 3-methyl-3-(2-fluoro-4-biphenylyl)-glycidate. The yield was 79%.

To a solution of 9.0 g of methyl 3-methyl-3-(2-fluoro-4-biphenylyl)-glycidate in a solvent mixture comprising 30 ml of dimethylsulfoxide and 20 ml of benzene was added with ice-cooling 5 ml of an ether solution of boron trifluoride. The mixture was brought back to room temperature, stirred for 2 hours and then poured into water, thereby effecting benzene extraction. The benzene layer was successively washed with water, aqueous sodium bicarbonate solution and water, and dried over anhydrous magnesium sulfate. Thereafter, the benzene was removed by distillation under reduced pressure to obtain 8.4 g of methyl 2-hydroxy-3-(2-fluoro-4-biphenylyl)-3-butenoate in the form of oil. The yield was 92%.

Elementary analysis: for $C_{17}H_{15}FO_3$ (286) — Calculated: C: 71.32%, H: 5.28%. Found: C: 71.11%, H: 5.40%.

EXAMPLE 5
Methyl 2-Hydroxy-3-(4'-fluoro-4-biphenylyl)-3-butenoate

A solution of 9.5 g of 4-acetyl-4'-fluorobiphenyl and 9.6 g of methyl chloroacetate in a solvent mixture comprising 20 ml of benzene and 10 ml of dimethylformamide was vigorously stirred, and 5.3 g of sodium methoxide was gradually added thereto in a nitrogen stream at below 8° C. over a period of 30 minutes. After stirring at 10° C. for 1 hour, at 25° C. for 1 hour and at 60° C. for 1 hour, the mixture was cooled and charged with water, thereby effecting benzene extraction. The benzene layer was washed with water and dried over anhydrous magnesium sulfate and, thereafter the benzene was removed therefrom by distillation under reduced pressure to obtain 10.1 g of methyl 3-methyl-3-(4'-fluoro-4-biphenylyl)-glycidate in the form of powder, m.p. 68.6°-70.2° C. The yield was 79% (calculated value).

IR (cm$^{-1}$) 1740, 1597, 1498, 1208, 823.

NMR (δ ppm) 1.70, 1.73 (3H, s, s,

3.42, 3.77 (3H, s, s, —CO$_2$CH$_3$), 3.42, 3.65 (1H, s, s,

To a solution of 9.0 g of methyl 3-methyl-3-(4'-fluoro-4-biphenylyl)-glycidate in a solvent mixture comprising 30 ml of dimethylsulfoxide and 20 ml of benzene was added with ice-cooling 5 ml of an ether solution of boron trifluoride. The mixture was brought back to room temperature, stirred for 2 hours and then poured into water, thereby effecting benzene extraction. The benzene layer was successively washed with water, aqueous sodium bicarbonate solution and water, and then dried over anhydrous magnesium sulfate and, thereafter the benzene was removed therefrom by distillation under reduced pressure to obtain 8.5 g of methyl 2-hydroxy-3-(4'-fluoro-4-biphenylyl)-3-butenoate. The yield was 94%.

Elementary analysis: for $C_{17}H_{15}FO_3$ — Calculated: C: 71.32%, H: 5.28%. Found: C: 71.11%, H: 5.01%.

IR (cm$^{-1}$) 3463, 1731, 1600, 1499, 1223, 1160, 831.

NMR (δ ppm) 3.71 (3H, s, —CO$_2$Me), 5.08 (1H, s,

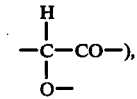

5.44, 5.55 (2H, s, s,

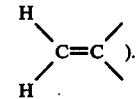

EXAMPLE 6
Isopropyl 2-Hydroxy-3-(4-cyclohexylphenyl)-3-butenoate

A solution of 20 g of 4-cyclohexylacetophenone and 26.5 g of isopropyl chloroacetate in 50 ml of benzene was vigorously stirred, and 21 g of sodium isopropoxide was gradually added thereto in a nitrogen stream at below 5° C. over a period of 1 hour. After stirring at 5° C. for 1 hour, at room temperature for 1 hour and at refluxing temperature for 1 hour, the mixture was cooled and charged with benzene and water, thereby effecting benzene extraction. The benzene layer was washed with water and dried over anhydrous sodium sulfate and, thereafter the benzene was removed therefrom by distillation under reduced pressure.

The resultant isopropyl 3-methyl-3-(4-cyclohexylphenyl)-glycidate was dissolved in 200 ml of dimethylformamide, and 15 ml of a 47% ether solution of boron trifluoride was added thereto with ice-cooling. After completion of the dropwise addition, the mixture was brought back to room temperature and, after stirring for 4 hours, the reaction liquid was poured into water and extracted with ethyl acetate. The ethyl acetate layer was washed with water and dried, thereafter the ethyl acetate was removed therefrom by distillation under reduced pressure to obtain 23 g of isopropyl 2-hydroxy-3-(4-cyclohexylphenyl)-3-butenoate in the form of a pale yellow oil. The yield was 75%.

Elementary analysis: for $C_{19}H_{26}O_3$ (302) — Calculated: C: 75.46%, H: 8.67%. Found: C: 75.18%, H: 8.50%.

EXAMPLE 7

Methyl 2-Hydroxy-3-(4-biphenylyl)-3-butenoate

To a solution of 8.0 g of methyl 3-methyl-3-(4-biphenylyl)-glycidate in 50 ml of dimethylacetamide was added dropwise with ice-cooling 7 ml of a 47% ether solution of boron trifluoride. After completion of the addition, the mixture was brought back to room temperature and, after stirring for 4 hours, was poured into water and extracted with ethyl acetate. The ethyl acetate layer was successively washed with water, aqueous sodium bicarbonate solution and water, and then dried over anhydrous magnesium. The ethyl acetate was removed by distillation under reduced pressure to obtain 6.0 g of methyl 2-hydroxy-3-(4-biphenylyl)-3-butenoate. The yield was 75%.

Elementary analysis: for $C_{17}H_{16}O_3$ (268) — Calculated C: 76.10%, H.: 6.01%. Found: C: 75.95%, H: 6.18%.

IR (cm$^{-1}$) 3460, 1731, 1596, 1242, 1208, 1112, 1078, 843.

NMR 3.72 (3H, s, —CO$_2$Me), 5.10 (1H, s,

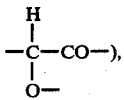

), 5.44, 5.56 (2H, s, s,

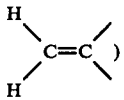

)

EXAMPLE 8

Methyl 2-Hydroxy-3-(3-benzoylphenyl)-3-butenoate

To a solution of 11.0 g of methyl 3-methyl-3-(3-benzoylphenyl)-glycidate in 50 ml of dimethylsulfoxide was added with stirring and ice-cooling 6 ml of a 47% ether solution of boron trifluoride. The mixture was brought back to room temperature and, after stirring overnight, poured into water and extracted with ethyl acetate. The ethyl acetate layer was successively washed with water, aqueous sodium bicarbonate solution and water, and then dried over anhydrous magnesium sulfate. The ethyl acetate was removed by distillation under reduced pressure. The resultant crude oily substance was purified by silica gel column chromatography to obtain 6.4 g of methyl 2-hydroxy-3-(3-benzoylphenyl)-3-butenoate. The yield was 58%.

Elementary analysis: for $C_{18}H_{16}O_4$ (296) — Calculated: C: 72.96%, H: 5.44%. Found: C: 73.08%, H: 5.31%.

EXAMPLE 9

Methyl 2-Hydroxy-3-(4'-fluoro-4-biphenylyl)-3-butenoate

To a mixture of 100 ml of isopropyl ether and 10.0 g of aluminum chloride was added dropwise with stirring a solution of 8.5 g of methyl 3-methyl-3-(4'-fluoro-4-biphenylyl)-glycidate in 40 ml of isopropyl ether. After completion of the addition, the mixture was refluxed with stirring for 5 hours, cooled and charged with dilute hydrochloric acid. After stirring for 20 minutes, the isopropyl ether layer is separated from the mixture, and the aqueous layer was extracted with isopropyl ether, and the extract was then combined with the separated isopropyl ether layer. The combined isopropyl ether layer was successively washed with water, aqueous sodium bicarbonate solution and water, and then dried over magnesium sulfate. The isopropyl ether was removed by distillation under reduced pressure, and the residue was purified by silica gel column chromatography to obtain 5.8 g of methyl 2-hydroxy-3-(4'-fluoro-4-biphenylyl)-3-butenoate. The yield was 58%.

Elementary analysis: for $C_{17}H_{15}FO_3$ (286) — Calculated: C: 71.32%, H: 5.28%. Found: C: 71.09%, H: 5.41%.

EXAMPLE 10

Ethyl 2-Hydroxy-3-(3-phenoxyphenyl)-3-butenoate

A solution of 9.7 g of 3-phenoxyacetophenone and 12.2 g of ethyl chloroacetate in 30 ml of ethyl ether was vigorously stirred, and 8.8 g of sodium ethoxide was gradually added thereto in a nitrogen stream at 5°-6° C over a period of 1 hour. After stirring at 6° C. for 1 hour, at 25° C. for 1 hour and at refluxing temperature for 1 hour, the mixture was cooled and charged with ether and water, thereby effecting ether extraction. The ether layer was washed with water and then dried over anhydrous sodium sulfate. The ether was removed by distillation under reduced pressure. The residue was dissolved in 150 ml of butyl ether, and the solution was charged with 12 g of aluminum chloride and refluxed with stirring at 80° C. for 5 hours. After cooling, the mixture was charged with dilute hydrochloric acid and, after stirring for 20 minutes, the butyl ether layer was separated, and the aqueous layer was extracted with butyl ether. The extract was combined with the separated butyl ether layer, and the combined layer was successively washed with water, aqueous sodium bicarbonate solution and water, and then dried over anhydrous magnesium sulfate. The butyl ether was removed by distillation under reduced pressure, and the residue was purified by silica gel column chromatography to obtain 4.5 g of ethyl 2-hydroxy-3-(3-phenoxyphenyl)-3-butenoate. The yield was 46%.

Elementary analysis: for $C_{18}H_{18}O_4$ (298) — Calculated: C : 72.46%, H : 6.08%. Found: C : 72.21%, H : 6.30%.

EXAMPLE 11 i. Methyl 3-Methyl-3-(4-cyclohexylphenyl)-pyruvate 5.0 Grams of methyl 2-hydroxy-3-(4-cyclohexylphenyl)-3-butenoate was dissolved in 30 ml of anhydrous methanol. Separately, a sodium methylate solution was prepared from 0.5 of metallic sodium and 20 ml of anhydrous methanol. The two solutions thus prepared were combined together, and the combined solution was refluxed for 30 minutes. The solution was cooled and charged with 2.5 ml of glacial acetic acid, and the mixture was distilled at a low temperature and under reduced pressure to remove the methanol therefrom. The the residue were added ethyl acetate and water, thereby effecting ethyl acetate extraction. The ethyl acetate layer was successively washed with water, aqueous sodium bicarbonate solution and water and dried over anhydrous magnesium sulfate. 4.2 Grams of crude crystals obtained by removing the ethyl acetate by distillation under reduced pressure was recrystallized from hexane to obtain 3.8 g of methyl 3-methyl-3-(4-cyclohexylphenyl)-pyruvate, m.p. 71.1°–72.2° C. The yield was 76% (theoretical value).

Elementary analysis: for $C_{17}H_{22}O_3$— Calculated: C : b 74.42%, H : 8.08%. Found: C : 74.28%, H : 9.20%.

ii. 3-Methyl-3-(4-cyclohexylphenyl)-pyruvic Acid

To a solution of 2.1 g of methyl 3-methyl-3-(4-cyclohexylphenyl)-pyruvate, which had been obtained in the foregoing (i), in 20 ml of methanol was added a solution of 1.0 g. of potassium hydroxide in 10 ml of methanol. The mixture was charged with 1 ml of water and stirred at room temperature for 1 hour. After completion of the reaction, the methanol was removed by distillation under reduced pressure, and the residue was charged with water and insoluble matter was removed therefrom by extraction with ethyl acetate. The extraction mother liquor was acidified with hydrochloric acid and extracted with ethyl acetate. The ethyl acetate layer was successively washed with water and saturated aqueous sodium chloride solution and then dried over anhydrous magnesium sulfate. 1.9 Grams of crude crystals obtained by removing the ethyl acetate by distillation under reduced pressure was recrystallized from benzene-hexane to obtain 1.7 g. of 3-methyl-3-(4-cyclohexylphenyl)-pyruvic acid, m.p. 100.5°–102.1° C. The yield was 84% (theoretical value).

Elementary analysis: for $C_{16}H_{20}O_3$ — Calculated: C : 73.82%, H : 7.74%. Found: C : 73.90%, H : 7.81%.

EXAMPLE 12 i. Methyl 3-Methyl-3-(3-phenoxyphenyl)-pyruvate 1.5 Grams of methyl 2-hydroxy-3-(3-phenoxyphenyl)-3-butenoate was dissolved in 20 ml of anhydrous methanol. Separately, a sodium methylate solution was prepared from 0.2 g of metallic sodium and 20 ml of anhydrous methanol. The two solutions thus prepared were combined together, and the combined solution was refluxed for 20 minutes. After cooling, the solution was charged with 1.5 ml of glacial acetic acid, and the methanol was removed therefrom by distillation. To the residue were added ethyl acetate and water, thereby effecting ethyl acetate extraction. The ethyl acetate layer was successively washed with water, aqueous sodium bicarbonate solution and water, and dried over anhydrous magnesium sulfate. The ethyl acetate was removed by distillation under reduced pressure to obtain 1.2 g of methyl 3-methyl-3-(3-phenoxyphenyl)-pyruvate in the form of a pale yellow oil. The yield was 80%.

Elementary analysis: for $C_{17}H_{16}O_4$— Calculated: C : 71.82%, H : 5.67%. Found: C : 71.90%, H : 5.80%.

ii. 3-Methyl-3-(3-phenoxyphenyl)-pyruvic Acid

To a solution of 0.8 g of methyl 3-methyl-3-(3-phenoxyphenyl)-pyruvate, which had been obtained in (i) of Example 12, in 10 ml of methanol, was added a solution of 0.8 g of potassium hydroxide in a mixture comprising 5 ml of methanol and 0.5 ml of water. The resulting mixture was stirred at room temperature for 30 minutes. After completion of the reaction, the methanol was removed from the reaction liquid by distillation under reduced pressure. The residue was charged with water, and insoluble matter was removed by extraction with ethyl acetate. The extraction mother liquor was acidified with hydrochloric acid and extracted with ethyl acetate. The ethyl acetate layer was successively washed with water and saturated aqueous sodium chloride solution, and then dried over anhydrous magnesium salfate. The ethyl acetate was removed by distillation under reduced pressure to obtain 0.6 g of 3-methyl-3-(3-phenoxyphenyl)l-pyruvic acid in the form of a pale yellow oil. The yield was 75%.

Elementary analysis: for $C_{16}H_{14}O_4$ — Calculated: C : 71.10%, H : 5.22%. Found: C : 70.98%, H : 5.28%.

EXAMPLE 13 i. Methyl 3-Methyl-3-(4-biphenylyl)-pyruvate

To a solution of 0.3 g of metallic sodium in 30 ml of anhydrous methanol was added a solution of 3.1 g of methyl 2-hydroxy-3-(4-biphenylyl)-3-butenoate in 10 ml of anhydrous methanol. The resulting mixture was refluxed for 30 minutes and then cooled, and thereto was added 3 ml of glacial acetic acid. The mixture was distilled at a low temperature and under reduced pressure to remove the methanol therefrom. To the residue were added ethyl acetate and water, thereby effecting ethyl acetate extraction. The ethyl acetate layer was successively washed with water, aqueous sodium bicarbonate solution and water, and dried over anhydrous magnesium sulfate. The ethyl acetate was removed by distillation under reduced pressure to obtain crude crystals. 3.0 Grams of the crude crystals was recrystallized from isopropyl alcohol to obtain 1.9 g of methyl 3-methyl-3-(4-biphenylyl)-pyruvate, m.p. 84.5°–86.5° C. The yield was 61% (theoretical value).

Elementary analysis: for $C_{17}H_{16}O_3$ — Calculated: C : 76.10%, H : 6.01%. Found: C : 76.01%, H : 6.13%.

ii. 3-Methyl-3-(4-biphenylyl)-pyruvic Acid

To a solution of 1.1 g of methyl 3-methyl-3-(4-biphenylyl)-pyruvate, which had been obtained in (i) of Example 13, in 20 ml of methanol was added a solution of 0.8 g of potassium hydroxide in 5 ml of methanol, and the resulting mixture was stirred at room temperature for 30 minutes. After completion of the reaction, the methanol was removed from the reaction mixture by distillation under reduced pressure. To the residue was added water, and insoluble matter was removed therefrom by extraction with ethyl acetate. The extraction mother liquor was acidified with hydrochloric acid and extracted with ethyl acetate. The ethyl acetate layer was successively washed with water and saturated aqueous sodium chloride solution, and then dried over anhydrous magnesium sulfate. The ethyl acetate was removed by distillation under reduced pressure to obtain curde crystals. 0.9 Gram of the crude crystals was recrystallized from benzene to obtain 0.75 g of 3-methyl-3-(4-biphenylyl)-pyruvic acid, m.p. 141.0°–143.2° C. The yield was 72% (theoretical value).

Elementary analysis: for $C_{16}H_{14}O_3$ — Calculated: C : 75.57%, H : 5.55%. Found: C : 75.48%, H : 5.61%.

EXAMPLE 14 i. Methyl 3-Methyl-3-(4'-fluoro-4-biphenylyl)-pyruvate

To a solution of 0.55 g of metallic sodium in 50 ml of anhydrous methanol was added a solution of 6.1 g of methyl 2-hydroxy-3-(4'-fluoro-4-biphenylyl)-3-butenoate in 20 ml of anhydrous methanol. The resulting mixture was refluxed for 20 minutes and then cooled, and the reaction liquid was charged with 5 ml of glacial acetic acid. The mixture was distilled at a low temperature and under reduced pressure to remove the methanol therefrom. To the residue were added ethyl acetate and water, thereby effecting ethyl acetate extraction. The ethyl acetate layer was successively washed with water, aqueous sodium bicarbonate solution and water. The ethyl acetate was removed by distillation under reduced pressure to obtain crude crystals. 5.4 Grams of the crude crystals was recrystallized from ethanol to obtain 4.6 g of methyl 3-methyl-3-(4'-fluoro-4-biphenylyl)-pyruvate, m.p. 100.0°–101.6° C. The yield was 75%.

Elementary analysis: for $C_{17}H_{15}FO_3$—Calculated: C : 71.32%, H : 5.28%. Found: C : 71.13%, H : 5.14%.

ii. 3-Methyl-3-(4'-fluoro-4-biphenylyl)-pyruvic Acid

To a solution of 1.2 g of methyl 3-methyl-3-(4'-fluoro-4-biphenylyl)-pyruvate, which had been obtained in (i) of Example 14, in 20 ml of methanol was added a solution of 1.0 g of potassium hydroxide in 10 ml of methanol, and the resulting mixture was stirred at room temperature for 30 minutes. After completion of the reaction, the methanol was removed from the reaction liquid by distillation under reduced pressure. To the residue was added water, and insoluble matter was removed therefrom by extraction with ethyl acetate. The extraction mother liquor was acidified with hydrochloric acid, and extracted with ethyl acetate. The ethyl acetate layer was successively washed with water and saturated aqueous sodium chloride solution, and then dried over anhydrous magnesium sulfate. The ethyl acetate was removed by distillation under reduced pressure to obtain crude crystals. 1.0 Gram of the crude crystals was recrystallized from benzene to obtain 0.9 g of 3-methyl-3-(4'-fluoro-4-biphenylyl)-pyruvic acid, m.p. 144.7°–145.9° C. The yield was 79%.

Elementary analysis: for $C_{16}H_{13}FO_3$ — Calculated: C : 70.58%, H : 4.81%. Found: C : 70.46%, H : 4.72%.

EXAMPLE 15

3-Methyl-3-(3-phenoxyphenyl)-pyruvic Acid 1.5 Grams of ethyl 2-hydroxy-3-(3-phenoxyphenyl)-3-butenoate was dissolved in 20 ml of anhydrous ethanol. Separately, a potassium ethylate solution was prepared from 0.35 g of metallic potassium and 20 ml of anhydrous ethanol. The two solutions thus prepared were combined together, and the combined solution was refluxed for 20 minutes. The reaction liquid was cooled and charged with 2 ml of water, and the mixture was stirred at room temperature for 30 minutes. The ethanol was removed from the mixture by distillation under reduced pressure. The residue was charged with water, and insoluble matter was removed therefrom by extraction with ethyl acetate. The extraction mother liquor was acidified with hydrochloric acid and extracted with ethyl acetate. The ethyl acetate layer was successively washed with water and saturated aqueous sodium chloride solution and then dried over anhydrous magnesium sulfate. The ethyl acetate was removed by distillation under reduced pressure to obtain 1.1 g of 3-methyl-3-(3-phenoxyphenyl)-pyruvic acid in the form of a pale yellow oil. The yield was 79%.

EXAMPLE 16

3-Methyl-3-(4-cyclohexylphenyl)-pyruvic Acid 3.0 Grams of isopropyl 2-hydroxy-3-(4-cyclohexylphenyl)-3-butenoate was dissolved in 50 ml of anhydrous isopropyl alcohol. Separately, 1.1 g of metalic potassium was dissolved in 100 ml of anhydrous isopropyl alcohol. The two solutions thus prepared were combined together, and the combined solution was refluxed for 20 minutes. To the solution was then added 2 ml of water, and the mixture was further refluxed for 5 minutes. Thereafter, the isopropyl alcohol was removed from the mixture by distillation under reduced pressure. The residue was charged with water, and insoluble matter was removed therefrom by extraction with ethyl acetate. The extraction mother liquor was acidified with hydrochloric acid and then extracted with ethyl acetate. The ethyl acetate layer was successively washed with water and saturated aqueous sodium chloride solution, and then dried over anhydrous magnesium sulfate. The ethyl acetate was removed by distillation under reduced pressure to obtain crude crystals. The crude crystals were recrystallized from benzene-hexane to obtain 2.15 g of 3-methyl-3-(4-cyclohexylphenyl)-pyruvic acid, m.p. 100.6°–102.5° C. The yield was 83%.

EXAMPLE 17 i. Methyl 3-Methyl-3-(2-fluoro-4-biphenylyl)-pyruvate

To a solution of 1.1 g of metallic sodium in 100 ml of anhydrous methanol was added a solution of 12.2 g of methyl 2-hydroxy-3-(2-fluoro-4-biphenylyl)-3-butenoate in 40 ml of anhydrous methanol, and the resulting mixture was refluxed for 20 minutes and then cooled. The reaction liquid was charged with 10 ml of glacial acetic acid, and the methanol was removed therefrom by distillation at a low temperature and under reduced pressure. The residue was charged with ethyl acetate and water, thereby effecting ethyl acetate extraction. The ethyl acetate layer was successively washed with water, aqueous sodium bicarbonate solution and water, and then dried over anhydrous magnesium sulfate. Thereafter, the ethyl acetate was removed by distillation under reduced pressure to obtain 9.0 g of methyl 3-methyl-3-(2-fluoro-4-biphenylyl)-pyruvate. The yield was 73%.

Elementary analysis: for $C_{17}H_{15}FO_3$—
Calculated: C : 71.32%, H : 5.28%.
Found: C : 71.21%, H : 5.40%.

ii. 3-Methyl-3-(2-fluoro-4-biphenylyl)-pyruvic Acid

To a solution of 2.4 g of methyl 3-methyl-3-(2-fluoro-4-biphenylyl)-pyruvate in 40 ml of methanol was added a solution of 2.0 g of potassium hydroxide in 20 ml of methanol, and the resulting mixture was stirred at room temperature for 30 minutes. Subsequently, the methanol was removed from the mixture by distillation under reduced pressure. The residue was charged with water, and insoluble matter was removed therefrom by extraction with ethyl acetate. The extraction mother liquor was acidified with hydrochloric acid and then extracted with ethyl acetate. The ethyl acetate layer was successively washed with water and saturated aqueous sodium chloride solution, and then dried over anhydrous magnesium sulfate. The ethyl acetate was removed by distillation under reduced pressure to obtain 1.8 g of 3-methyl-3-(2-fluoro-4-biphenylyl)-pyruvic acid. The yield was 79%.

Elementary analysis: for $C_{16}H_{13}FO_3$ — Calculated: C : 70.58%, H : 4.81%. Found: C : 70.39%, H : 5.01%.

EXAMPLE 18 i. Ethyl 3-Methyl-3-(3-benzoylphenyl)-pyruvate

To a solution of 0.5 g of metallic sodium in 50 ml of anhydrous ethanol was added a solution of 3.0 g of ethyl 2-hydroxy-3-(3-benzoylphenyl)-3-butenoate in 20 ml of anhydrous ethanol. The resulting mixture was refluxed for 20 minutes and then cooled. The reaction liquid was charged with 5 ml of glacial acetic acid, and the ethanol was removed therefrom by distillation at a low temperature and under reduced pressure. The residue was charged with ethyl acetate and water, thereby effecting ethyl acetate extraction. The ethyl acetate layer was successively washed with water, aqueous sodium bicarbonate solution and water, and then dried over anhydrous magnesium sulfate. Thereafter, the ethyl acetate was removed by distillation under reduced pressure to obtain 2.2 g of ethyl 3-methyl-3-(3-benzoylphenyl)-pyruvate. The yield was 73%.

Elementary analysis: for $C_{19}H_{18}O_4$ — Calculated: C : 75.53%, H : 5.85%. Found: C : 75.32%, H : 5.71%.

ii. 3-Methyl-3-(3-benzoylphenyl)-pyruvic Acid

To a solution of 2.2 g of ethyl 3-methyl-3-(3-benzoylphenyl)-pyruvate in 20 ml of methanol was added a solution of 1.0 g of potassium hydroxide in 10 ml of methanol, and the resulting mixture was stirred at room temperature for 30 minutes. Subsequently, the methanol was removed from the mixture by distillation under reduced pressure. The residue was charged with water, and insoluble matter was removed therefrom by extraction with ethyl acetate. The extraction mother liquor was acidified with hydrochloric acid and then extracted with ethyl acetate. The ethyl acetate layer was successively washed with water and saturated aqueous sodium chloride solution, and then dried over anhydrous magnesium sulfate. The ethyl acetate was removed by distillation under reduced pressure to obtain 1.6 g of 3-methyl-3-(3-benzoylphenyl)-pyruvic acid. The yield was 79%.

Elementary analysis: for $C_{17}H_{14}O_4$ — Calculated: C : 72.33%, H : 5.00%. Found: C : 72.60%, H : 5.18%.

What we claim is:

1. A process for preparing a 3-methyl-3-(substituted aryl)-pyruvic acid compound of the general formula,

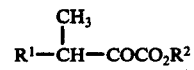

wherein $R^1$ represents 4-biphenylyl, 4-cyclohexylphenyl, 3-phenoxyphenyl, 4'-fluoro-4-biphenylyl, 2-fluoro-4-biphenylyl or 3-benzoylphenyl group, and $R^2$ represents a lower alkyl group or its corresponding free acid, which comprises treating a glycidic acid ester compound of the general formula,

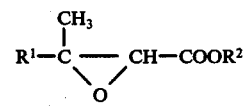

wherein $R^1$ and $R^2$ are individually as defined above with a Lewis acid, thereby to form a compound of the general formula,

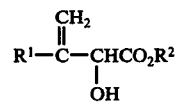

wherein $R^1$ and $R^2$ are individually as defined above; treating the thus resulted compound in an alchohol with an alkali metal alcoholate thereby to form 3-methyl-3-(substituted aryl)-pyruvic acid ester of the general formula,

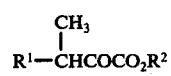

wherein $R^1$ and $R^2$ are individually as defined above and, if desired, saponifying said ester to yield a compound of the general formula,

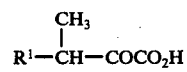

wherein $R^1$ is as defined previously.

2. A process as claimed in claim 1, wherein the Lewis acid is selected from the group consisting of boron trifluoride, aluminum chloride and zinc chloride.

3. A process as claimed in claim 1, wherein the reaction of the glycidic acid ester with the Lewis acid is conducted in a non-protonic polar solvent.

* * * * *